(12) United States Patent
Jewett et al.

(10) Patent No.: US 8,191,803 B2
(45) Date of Patent: Jun. 5, 2012

(54) AUTOMATIC WASHING DEVICE WITH FLUIDIC OSCILLATOR

(75) Inventors: Warren R. Jewett, Cary, NC (US); Thomas E. Plowman, Raleigh, NC (US); Craig A. Dupree, Raleigh, NC (US); Matthew D. Khare, Willow Spring, NC (US)

(73) Assignee: Fluidic Technologies, Inc., Cary, NC (US)

( * ) Notice: Subject to any disclaimer, the term of this patent is extended or adjusted under 35 U.S.C. 154(b) by 185 days.

(21) Appl. No.: 12/709,189

(22) Filed: Feb. 19, 2010

(65) Prior Publication Data
US 2011/0203047 A1 Aug. 25, 2011

(51) Int. Cl.
  *B05B 1/08* (2006.01)
  *B05B 1/02* (2006.01)
  *B05B 1/00* (2006.01)
(52) U.S. Cl. ............... 239/589.1; 239/596; 239/597; 239/598; 239/599
(58) Field of Classification Search ............ 239/589.1, 239/596–599, 601; 137/808, 809, 811, 833
See application file for complete search history.

(56) References Cited

U.S. PATENT DOCUMENTS

| | | | |
|---|---|---|---|
| 4,662,568 A | 5/1987 | Bauer | |
| RE33,448 E | 11/1990 | Bauer | |
| RE33,605 E | 6/1991 | Bauer | |
| 5,129,585 A * | 7/1992 | Bauer | 239/589.1 |
| 6,110,292 A | 8/2000 | Jewett et al. | |
| 6,176,941 B1 | 1/2001 | Jewett et al. | |
| 7,070,129 B1 | 7/2006 | Raghu et al. | |
| 2004/0164189 A1 | 8/2004 | Berning et al. | |
| 2006/0108442 A1* | 5/2006 | Russell et al. | 239/102.1 |
| 2008/0099050 A1 | 5/2008 | Barnhill et al. | |

FOREIGN PATENT DOCUMENTS
WO  WO 2008/054907 A  5/2008

OTHER PUBLICATIONS

International Search Report and Written Opinion issued by European Patent Office for corresponding international application PCT/US2011/025259 mailed Sep. 22, 2011.

* cited by examiner

*Primary Examiner* — Darren W Gorman
(74) *Attorney, Agent, or Firm* — Frommer Lawrence & Haug LLP; Ronald R Santucci (57) ABSTRACT

An automatic washing device includes a plurality of fluidic oscillators arranged on the periphery of a rotating drum. The fluidic oscillators emit a pulsatile stream of fluid at a predetermined angle through a slit that is perpendicular or at an angle to a longitudinal axis of the oscillator. The automatic washing device can remove microorganisms from the pliant epidermal surface of a human hand that comprises brushlessly scrubbing the pliant epidermal surface of the human hand with a plurality of cleansing fluids.

7 Claims, 7 Drawing Sheets

RELATED ART

AUTOMATIC WASHING DEVICE WITH FLUIDIC OSCILLATOR

BACKGROUND OF THE INVENTION

1. Technical Field

This invention relates to an automatic washing device. More particularly, this disclosure relates to a device for automatically washing hands that uses fluidic oscillators.

2. Description of Related Art

The cleansing of objects, in particular as it relates to the washing of human and animal body parts and skin for the purpose of reducing pathogens that may be transmitted to other objects or parties, can be particularly useful to the medical, surgical and food handling communities. The ability to remove pathogens such as, for example, both transient *Escherichia coli* (*E. coli*), *Salmonella* and resident *Staphylococcus aureus* pathogens can reduce the transmittal of such bacteria. Transient micro-organisms are generally found on the surface of the skin and are picked up either through the air or by contact with a physical object. For example, the transient micro-organisms may be acquired by handling of raw meats and from previously contaminated surfaces and are generally readily washed off by any number of washing techniques. The resident microorganisms found embedded in the pores and folds of the skin and tissues may be more difficult to remove than from exposed surfaces. Fast food establishments are particularly prone to passing on such pathogens because large quantities of food are handled and served to the public and because of the lack of adequate training and education in hygiene required of food handling personnel.

The critical care of injured or wounded personnel can be improved based on the degree to which pathogens, and non-pathogens that can become pathogenic in the wound environment, can be eliminated from wounds prior to their being operated on, consequently minimizing the incidence of sepsis, infection, and disease. Until the 20th century many war deaths could be attributed to lack of sanitation and infection of, often, non-critical wounds.

Conventional scrubbing of skin, for example with cloths or brushes and soaps (both ordinary and antibacterial), is only moderately effective when a short procedure, such as is normally employed by marginally dedicated people, is used. Typically, about 50 percent removal occurs. Surgical scrubs, which may last as long as 5-15 minutes, depending on the diligence and experience of the personnel, may remove as much as 90-98 percent of the transient micro-organisms, but very few, if any, of the resident micro-organisms. Frequent scrubbing can result in "dish-pan-hands" syndrome, redness, irritation and epidermal loss, which is associated with abrasion as well as increased sensitivity to chemicals when the chemicals are forcibly scrubbed on the skin. Moreover, considerable time is consumed in thorough hand washing. When an 8 minute scrub is required even before a short procedure, this can limit the number of procedures that can be conducted during any given day. Automatic hand washing devices can improve the efficacy of the washing process and also reduce the time to achieve removal of pathogens as compared to manual washing.

Some automatic hand washers use nozzles to deliver fluids to clean the skin. The nozzles may be mechanical or electrical. A nozzle takes a steady input stream of fluid at a certain pressure and delivers a steady stream of fluid for cleansing at the same or different pressure. A Fluidic oscillator also may be mechanical or electrical. A fluidic oscillator takes a steady input stream of fluid at a certain pressure and delivers the fluid for cleansing at the same or different pressure in a sweeping action. However, a fluidic oscillator is distinguished from a nozzle in that the fluidic oscillator can deliver a pulsatile output stream of fluid swept in a fan shaped spray.

Pulsating jets of water that pulse at a frequency that is in resonance with the dynamic response of the human epidermis, about 20-25 Hz, can cause the skin to resonantly vibrate wherein the pores, ridges and crevices of the skin alternately expand and contract in such a way as to loosen resident pathogens as well as embedded oils, greases, and dirt/solid particles. High pressure (e.g., in the range of 50-80 psi) water jets can flush the loosened matter away while depositing antibacterial chemicals as desired, in effect scrubbing the dermis without the abrasive action of brushes.

DETAILED DESCRIPTION

The following description is primarily concerned with "hand and forearm" washing of human limbs. However, the disclosed apparatus and method is applicable to any epidermal sites, including, but not limited to, proposed surgical sites. In addition, the apparatus and method can be applied to cleansing of the skin or surface of a variety of living or non-living beings including fish, poultry, mammals, vegetables, food stuffs, and others. Any pliant, porous or non-porous, surfaces that have resonant vibratory characteristics can benefit from the cleansing of the present apparatus and method. Such surfaces are exemplified by leather, upholstery, plastics and rubbers. Additional applications for the disclosed techniques include, but are not limited to, wound debridement and cleaning and sanitizing meat in an abattoir.

The disclosed apparatus and method comprises directing a plurality of oscillating jets of a given liquid onto a selected area of skin to be cleansed in a predetermined manner in such a way as to effect a mechanical debridement cleansing of said skin. A number of different liquids are applied serially during the period of the cleansing cycle. Clean warm water can be applied first that wets the skin surface and removes large surface particles and moistens and softens the skin and warms any fats, oils and/or greases to reduce their viscosity or to fluidize them to such an extent that makes them more readily removed. The second liquid may be an aqueous antibacterial soap or disinfecting solution which by its surfactant action removes said oils, fats and greases, and by its sweeping and pulsatile mechanical debridement action detaches micro-organisms from both the surface and the pores and folds. The third liquid may be plain water or may be a solution of water and emollients which rinse the skin, flush away the microorganisms, particles, fats, etc. and the dirty soap or disinfecting solution. The emollient ingredient is used to condition the skin to prevent chapping or to facilitate putting on surgical gloves and the like.

Figure 1:
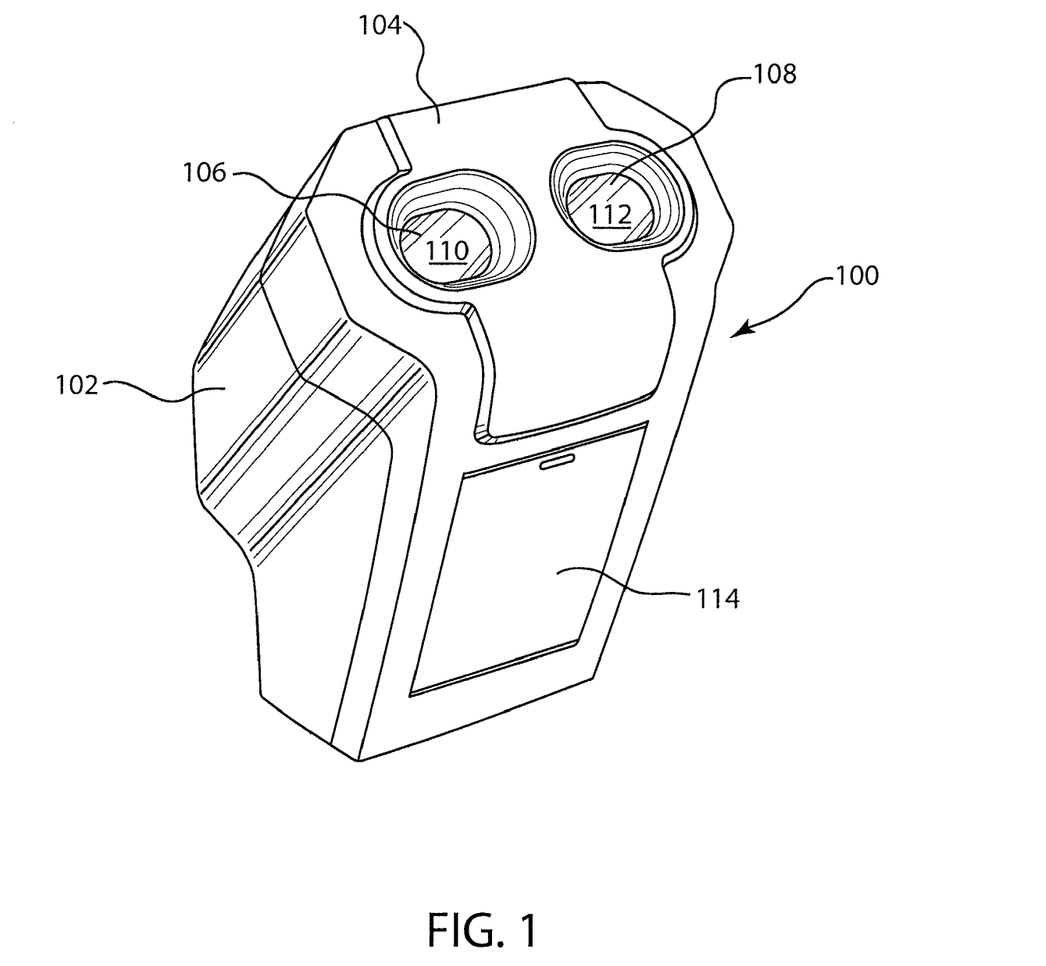
FIG. 1 illustrates an embodiment of the automatic hand washing apparatus of the present disclosure.

FIG. 1 is an illustration of an embodiment of a handwashing apparatus 100. A housing 102 may be fabricated from a synthetic polymeric resin such as polyvinyl chloride, polyurethane, polycarbonate, polyethylene, metal, or other suitable material. The front panel 104 of housing 102 includes two apertures 106 and 108 of a size and dimension to receive the hand, wrist and portion of a human forearm. Apertures 106 and 108 give entry to wash chambers 110, 112 respectively. Door 114 in housing 100 provides access to disposable containers of cleansing agents and other solutions.

Figure 2:
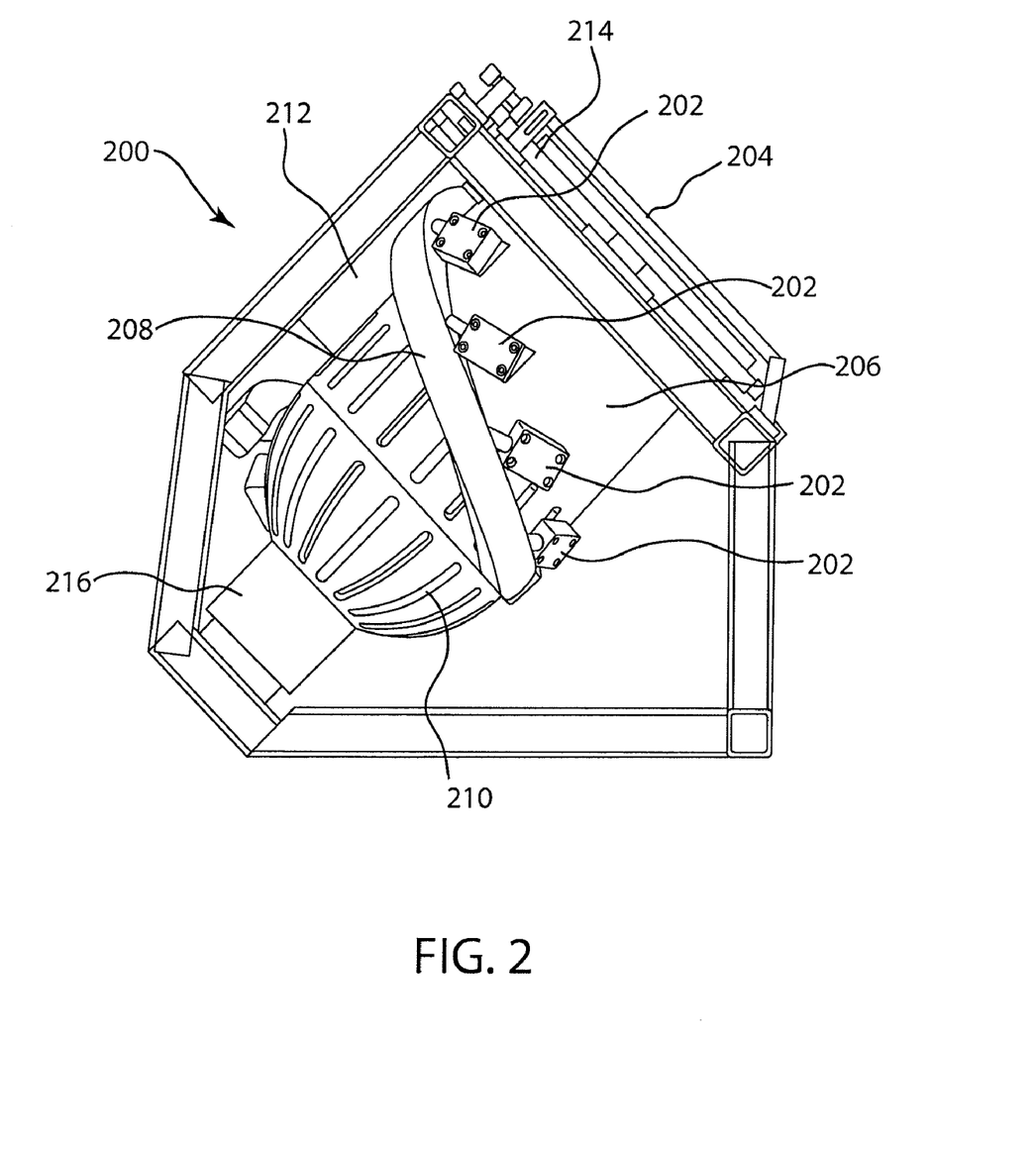
FIG. 2 illustrates a washing chamber that may be used in an automatic hand washer.

FIG. 2 is an illustration of an embodiment of a wash chamber 200. While multiple wash chamber apertures 106, 108 were shown in FIG. 1, a single wash chamber aperture 204 may be used depending on the desired application. Wash chamber 200 includes a wash chamber housing 206, which may be a substantially hollow cylindrical drum. In an implementation, the wash chamber housing can be rotatable about its axis. A plurality of fluidic spray oscillators 202 are mounted on the periphery of wash chamber housing 206. In a particular implementation, fluidic spray oscillators 202 are mounted in a helical pattern around the periphery of wash chamber housing 206. That is, the fluidic spray oscillators 202 are arrayed circumferentially in a spiral pattern along the outside shell of a rotating wash chamber housing 206.

Rotation of the cylinders during the wash cycle can assure that every aspect of the dermis is repeatedly exposed to the mechanical cleansing and debridement action of fluid emitted by the oscillators. Fluid exits the oscillators in a fan pattern composed of a sweeping arc of liquid droplets emitted at frequencies known to promote a trampoline effect on the dermis. It is this trampoline phenomenon on resilient surfaces, as the dermis, that can facilitate thorough cleaning.

One or more fluidic containment oscillators (not shown) may be mounted in a fixed array at a proximal end 214 opposite aperture 204 of each cylinder. These oscillators are distinct in geometry and function from the wash oscillators 202. When in operation, fluid exiting the containment oscillators can provide a fluid shield to aid in decreasing fluid splash-out from the wash chamber housing.

The array of fluidic spray oscillators 202 is supplied with fluids through a rotary fluid coupling 216 coupled to a fluid supply line 208. Fluid supply line 208 is coupled to each fluidic spray oscillator 202 and, when in operation, supplies fluid to an entry port of each fluidic spray oscillator. A single fluid supply line 208 may be used. Fluidic spray oscillators 202 are mounted over openings (not shown) in the wall of the wash chamber housing 206 so that fluid exiting the fluidic spray oscillator can enter into the cavity of the wash chamber housing 206.

Openings in a distal end 210 of the cylinders provide drainage for the expended washing and cleansing solutions. A motor 212 can provide the rotary motion for the cylinders. Additional features may be included to facilitate the automatic washing process. An optional detector can be incorporated into the hand washer to detect the insertion of a hand or other object into the washing chamber. The detector can be optical, magnetic, or other known method for detecting an object and initiating the washing apparatus.

Wash chamber 200 can be enclosed in a shell that provides hot and cold water inputs, cleanser storage, electrical connections, and appropriate plumbing. As a safety feature, multiple cylinders can be linked to the motor through a drive mechanism that allows for both normal rotation as well as stall in the case of a mechanical obstruction. A microprocessor can control the timing and intervals at which water of appropriate temperature, cleansing agents, and lotions are introduced into the cylinders. Timing and frequency of these and the rate of cylinder rotation can be independently programmed to meet specific needs of the user.

A hand washing system with this arrangement can require fewer fluidic spray oscillators than prior designs to achieve complete wash coverage and consume less water than convention washing systems.

Figure 3:
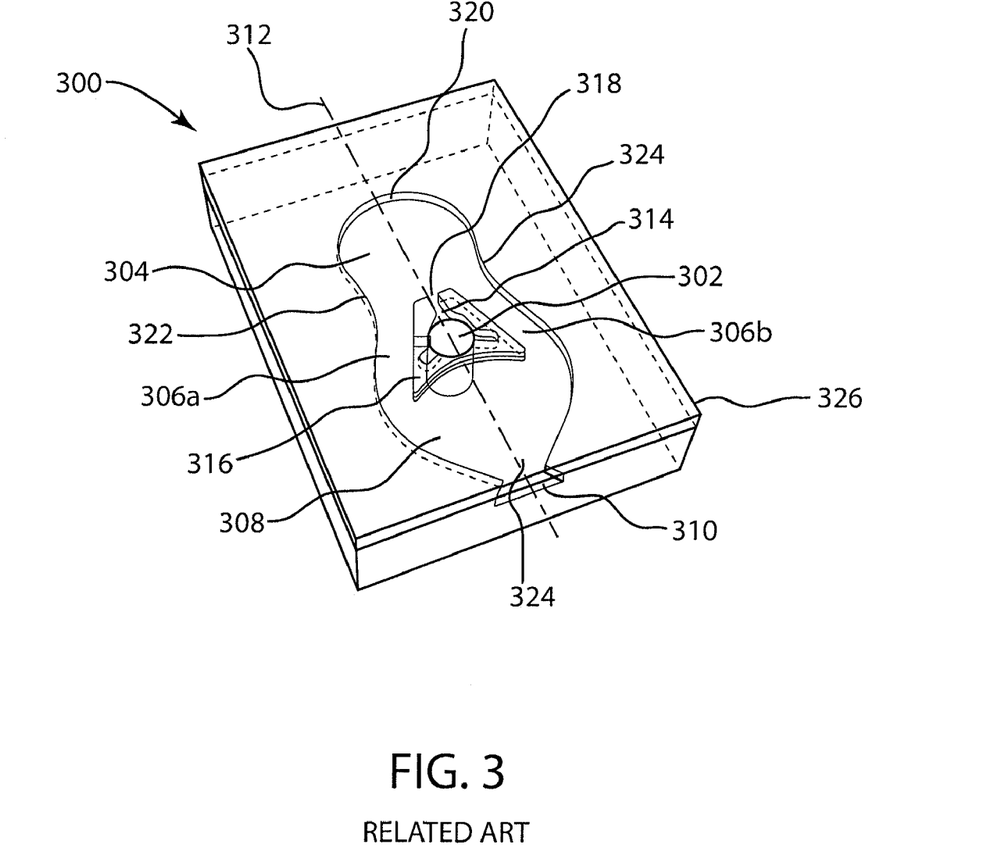
FIG. 3 illustrates a fluidic spray oscillator having an output spray that is along the axis of the path of fluid flow into the output chamber.

FIG. 3 is an illustration of a conventional fluidic spray oscillator 300 with a cover 326 through which the inner geometry can be seen. A fluidic spray oscillator is a non-electrical device that receives an input stream of fluid and delivers a pulsatile spray of fluid droplets in a sweeping fan pattern. Briefly, the oscillator is a two chamber hydraulic device that can output a sinusoidal pattern of fluid at a specific frequency and droplet size.

The concept of operation of a fluidic spray oscillator involves the following steps. First, a stream of fluid introduced through an inlet port 302 is directed into a generally circular input chamber 304 by means of a generally U-shaped channel 314. U-shaped channel 314 is part of an overall flow divider section 316. Fluid entering the common inlet/outlet opening 318 impinges a sidewall at the proximal end 320 of the fluid spray oscillator and is caused to form two swirling vortices that alternate in strength such that flow is back-directed out of common inlet/outlet opening 318 of input chamber 304.

Downstream of the common inlet and outlet opening 318 of oscillation chamber 304, the sidewalls 322 and 324 of the fluid spray oscillator diverge such that sidewall 322 along with flow divider 316 forms an outlet passage 306b from the oscillator, whereas sidewall 324 along with flow divider 316 forms an outlet passage 306a. The back-directed flow exiting input chamber 304 exits along one of two passages 306a, 306b to an output chamber 308.

Passages 306a, 306b deliver fluid into output chamber 308 in opposite rotational senses. The flows into output chamber 308 from passages 306a, 306b produce an output vortex in the output chamber that alternately rotates first in a clockwise direction and then in a counter-clockwise direction. The droplets of fluid in the output cortex are swept back and forth across a slit opening 310 at the distal end 324 of the output chamber 308. Slit opening 310 is arranged in a sidewall 312 of fluidic spray oscillator 300, transverse to a longitudinal axis 312 of the fluidic spray oscillator. In the fluidic spray oscillator of FIG. 3, fluid is discharged along the axis of the path of fluid flow into the output chamber.

At each point across outlet slit opening 310 there is a summation of flow velocity vectors from the output vortex that determines the overall shape of the issued spray pattern from outlet slit opening 310. In addition to dimensions of slit 308, the spray frequency and droplet size is dependent on the vector sum of a first vector, tangential to the output vortex and a function of the spin velocity, and a second vector, directed radially from the vortex and determined by the static pressure in the chamber. The resultant fluid spray issues from exit slit opening 310 in an almost sinusoidal manner.

Figure 4A:
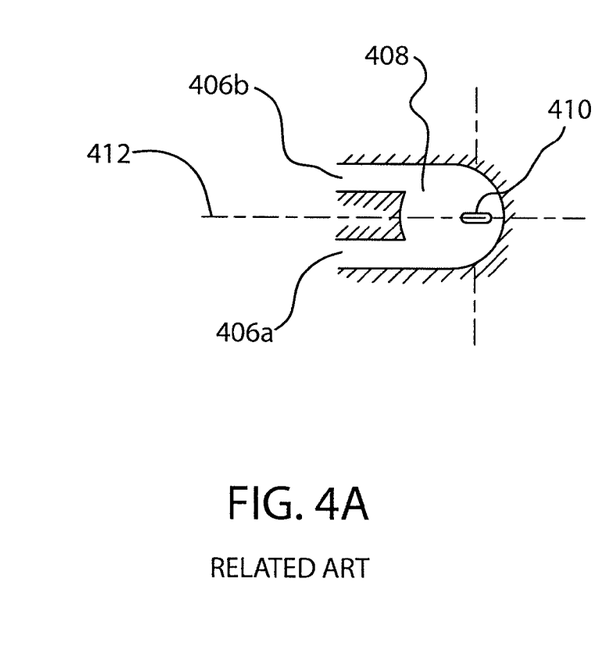
FIGS. 4A-4B illustrate a fluidic spray oscillator having an output spray that is perpendicular to the path of fluid flow into the output chamber.

FIG. 4A is an illustration of a portion of an embodiment of a fluidic spray oscillator having a exit slit 410 in a bottom (floor) surface of the output chamber 408 that ejects fluid droplets in a sinusoidal pattern. In fluidic spray oscillator of FIG. 4, fluid is discharged perpendicular to the path of flow into the output chamber. This embodiment may be referred to as a "side-shooter" as the fluid is ejected at right angles to the path of the fluid flow within the oscillator.

Figure 4B:
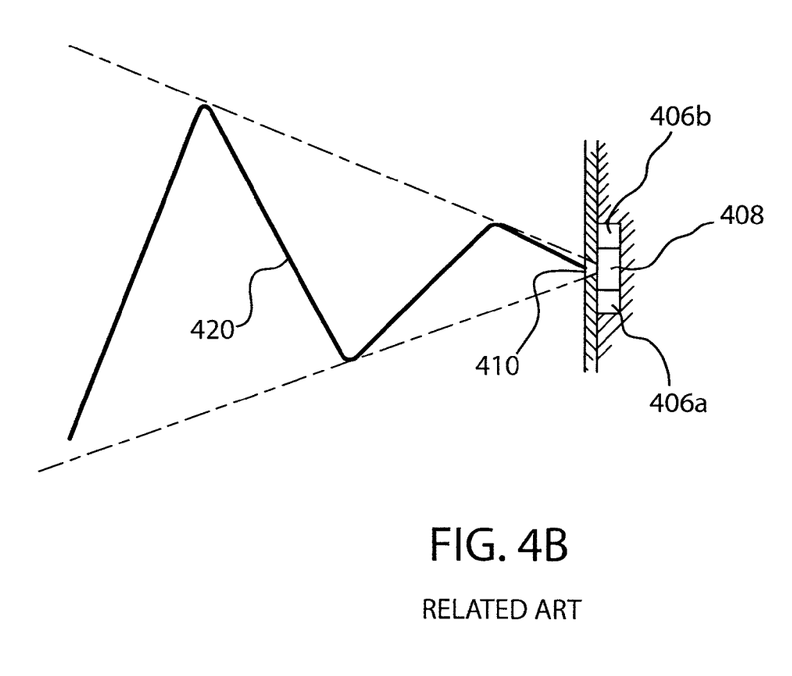

In the embodiment of FIG. 4A, the output chamber 410 receives alternating fluid pulses from passages 406a, 406b and delivers a planar or fan shaped swept pattern from an exit slit 410. Exit slit 410 is formed in the floor (or ceiling) of output chamber 408 rather than being defined in the end wall thereof as in the embodiment of FIG. 3. Exit slit 410 is aligned parallel to central axis 412 of the fluidic spray oscillator and extends along the radius of the alternating vortex in the output chamber. Because the spin velocity of a vortex varies at different radial points, the fluid velocity varies along the length of exit slit 410. As shown in FIG. 4B, the result renders the issued spray pattern waveform 420 asymmetric into the plane of the drawing in FIG. 4B, the asymmetry being greater for longer outlet openings.

A side-shooter fluidic spray oscillator having an exit slit on a bottom (floor) surface has an advantage in an automatic washing system because the fluidic oscillator does not have to be mounted perpendicular to the washing chamber. The exit slit also could be on a top (ceiling) surface of the fluidic spray oscillator. The side-shooter fluidic spray oscillator can be mounted to lie flat on the washing chamber and make the automatic washing system more compact.

Figure 5A:
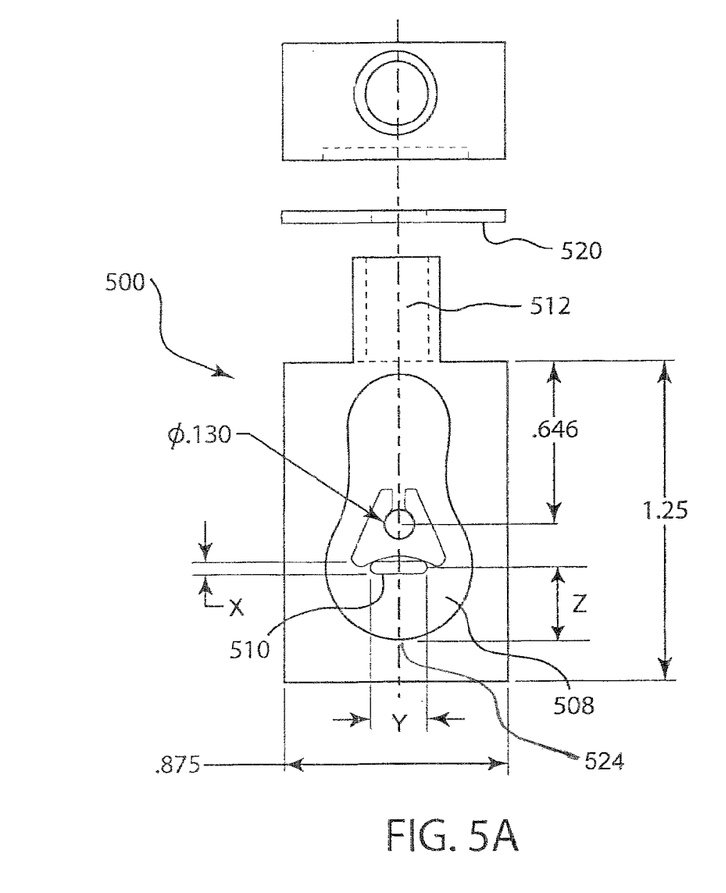
FIGS. 5A-5B illustrate a fluidic spray oscillator having an output spray that is perpendicular to the path of fluid flow into the output chamber in accordance with the present disclosure.
Figure 5B:
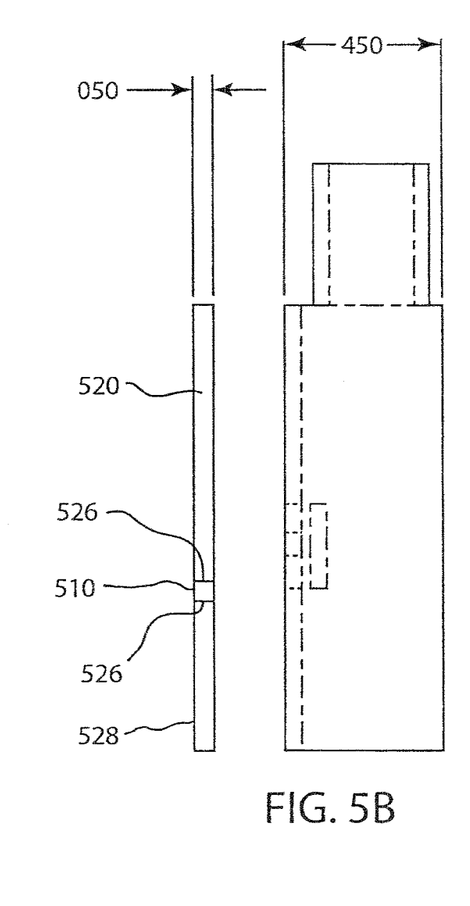

FIGS. 5A, 5B are an illustration of a side-shooter fluidic spray oscillator 500 that may be used in an automatic hand washer. FIG. 5A illustrates the fluidic spray oscillator with the cover 520 removed so the internal geometry may be seen. Similar to FIG. 4, exit slit 510 is formed in the floor (or ceiling) of output chamber 508 rather than being defined in the end wall thereof as in the oscillator of FIG. 3. However, in the disclosed fluidic spray oscillator the exit slit 510 is situated perpendicular or transverse to the long central axis 512 of the oscillator 500. The sidewalls 526 of exit slit 510 are perpendicular to the outside surface 528 of the fluidic spray oscillator.

The orientation and positioning and dimensions of exit slit 510 in output chamber 508 affect the characteristics of the pulsatile fluid ejected from the spray oscillator. FIGS. 5A and 5B provide a particular embodiment having dimensions for a fluidic spray oscillator of the present design. However, the dimensions of the fluidic oscillator 500 are not limited to the illustrated dimensions. In the embodiment illustrated, exit slit 510 has width, X, in the range of 0.03" to 0.06", or 0.05". Exit slit 510 has a length, Y, in the range of 0.25" to 0.46", or 0.4". The center of exit slit 510 is located, from distal end 524, a distance, Z, in the range of 0.3" to 0.43", or 0.425". Choice of combinations of these dimensions determines an output spray having a desired fluid drop size, width of spray fan, and pattern.

The operation of the fluidic spray oscillator is similar to that as described above with respect to FIG. 4. In contrast to the output spray pattern of the oscillator of FIG. 4, the transverse orientation and positioning of exit slit 510 results in a sinusoidal pattern of fluid droplets exiting the oscillator of FIG. 5 that is substantially symmetrical and of substantially equal distributed force.

Figure 6A:
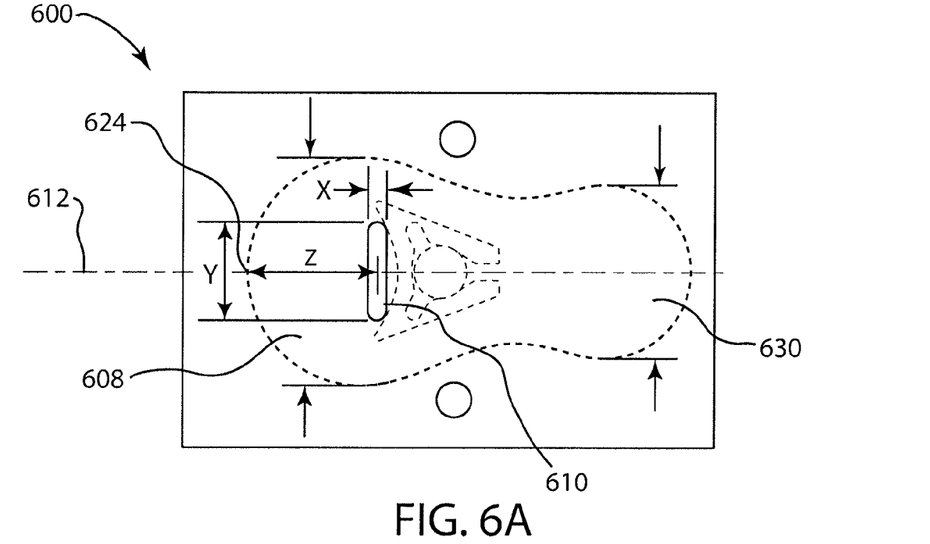
FIGS. 6A-6B illustrate another embodiment of a fluidic spray oscillator having an output spray that is at an angle to the path of fluid flow into the output chamber in accordance with the present disclosure.
Figure 6B:
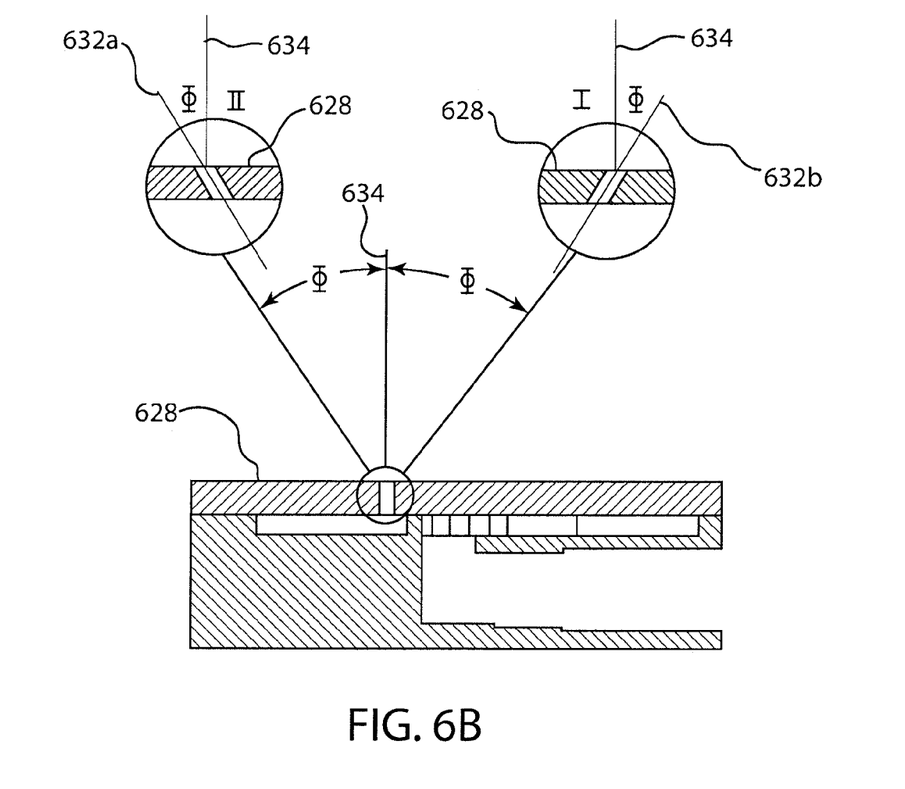

FIGS. 6A, 6B are an illustration of a side-shooter fluidic spray oscillator 600 that may be used in an automatic hand washer. Fluidic spray oscillator 600 is similar to that in FIGS. 5A-5B in that exit slit 610 is formed in the floor (or ceiling) of output chamber 608 and is situated perpendicular or transverse to the long central axis 612 of the oscillator 600. However, in the embodiment of FIG. 6, exit slit 610 is oblique with respect to outside surface 628. Exit slit 610 can be angled in toward either input chamber 630 as shown in insert I, or towards output chamber 628 as shown in insert II.

In an implementation, the angle, $\Phi$, of the centerline 632a or 632b of the exit slit is in the range of 30 to 45 degrees with respect to a perpendicular 634 to outside surface 628. In this range, the spray emitted from the output slot is at a pre-set angle to the fluid flow in the output chamber but not substantially thicker than the spray emitted when the exit slit walls are perpendicular to the output surface of the fluidic oscillator.

In the embodiment illustrated, exit slit 610 has width, X, in the range of 0.03" to 0.06", or 0.05". Exit slit 610 has a length, Y, in the range of 0.25" to 0.46", or 0.4". The center of exit slit 610 is located, from the distal end 624, a distance, Z, in the range of 0.3" to 0.43", or 0.425". Choice of combinations of these dimensions determines an output spray having a desired fluid drop size, width of spray fan, and pattern.

Figure 7:
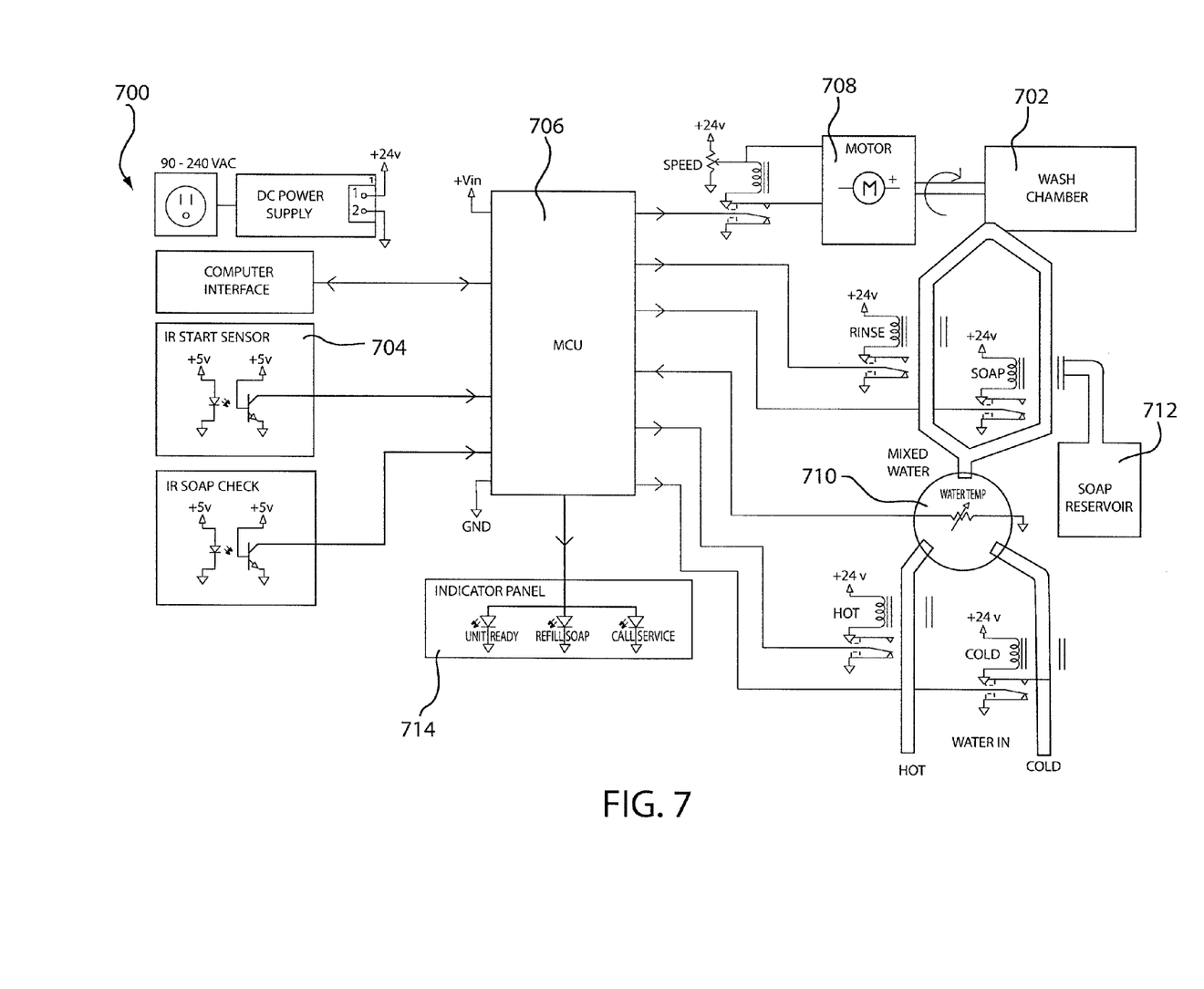
FIG. 7 illustrates a circuit for controlling an automatic hand washer.

FIG. 7 illustrates an arrangement of the electrical/fluidic circuit 700 for an automatic hand washer. Insertion of the hands into the wash chamber 702 can automatically begin the wash cycle by activating a detection sensor 704. The detection sensor 704 can be an optical sensor, magnetic sensor, capacitive or inductive reactance sensor or other proximity sensing device. In response to detection of the insertion of hands into the wash chamber, a microprocessor controller 706 can activate a motor 708 or other device to initiate rotation of the chamber (or chambers) into which the hands have been placed. The microprocessor controller can regulate, in sequence, the introduction of water (hot and cold) at the proper temperature and pressure 710 and antibacterial cleansing agents and/or lotion 712. The mechanical effect of fluid delivered through the fluidic spray oscillators can enhance the cleaning effectiveness. Removal of microorganisms and foreign matter may be achieved in a 10 to 15 second wash cycle. An indicator panel 714 may be included to provide visual indication of the operation of the automatic hand washer. As noted above, the washing chamber also can utilize a fluidic water shield at the proximal end of the wash cylinders which serves to minimize splash-out.

A radio frequency identifier tag (RFID) associated with a user may be detected by the automatic hand washer. The microprocessor can detect a particular user of the automatic hand washer. Information related to the particular user's usage of the automatic hand washer may be stored at the hand washer or transmitted to a central location or another automatic hand washer. The information may include the user's identification, date, time of day, length of usage or other information to assure compliance to proper hand washing requirements. In one embodiment, each automatic hand washer may include a transmitter to transmit the user information. In another embodiment, the automatic hand washer can include a receiver for receiving information related to a particular user. The automatic hand washer can include an indicator or other alerting device to notify the user or other personnel of compliance requirements.

Other implementations are within the scope of the following claims.

The invention claimed is:
1. A fluidic oscillator, comprising:
a fluid entry port to receive an entry fluid stream;
a first chamber coupled to the fluid entry port to receive the entry fluid stream, the first chamber having a shape to cause the entry fluid stream to form two swirling vortices that alternate in strength when the entry fluid stream enters the first chamber;
a second chamber fluidically coupled to the first chamber by two fluid paths, when in operation, the two swirling vortices direct fluid to flow out of the first chamber to the second chamber along the two fluid paths, the flow in the fluid paths varying in strength according to the alternat- ing forces of the swirling vortices, the variation in forces causing a fluid vortex to form in the second chamber and cause the vortex to spin in alternating directions; and an exit slit, having a length dimension greater than a width dimension thereof, through a bottom surface of the second chamber, the length of the exit slit being transverse to a longitudinal axis of the oscillator, wherein, when in operation, fluid in the second chamber exits through the exit slit in the bottom surface perpendicular to the path of fluid flow into the second chamber, and the fluid exits in a pattern dependent on the dimensions and location of the exit slit.

2. The fluidic oscillator of claim 1, wherein sidewalls of the exit slit are perpendicular to the bottom surface of the second chamber.

3. The fluidic oscillator of claim 1, wherein a width of the exit slit is in the range of 0.03 inches to 0.06 inches, a length of the exit slit is in the range of 0.25 inches to 0.46 inches; and a centerline of the exit slit is in the range of 0.3 inches to 0.43 inches from a distal end of the fluidic oscillator, said distal end located where the longitudinal axis intersects a periphery of the second chamber.

4. The fluidic oscillator of claim 3, wherein the length of the exit slit is approximately 0.4 inches;

the width of the exit slit is approximately 0.05 inches; and the centerline of the exit slit is approximately 0.425 inches from the distal end.

5. The fluidic oscillator of claim 1, wherein a centerline of the exit slit is at an oblique angle to a perpendicular to the bottom surface of the second chamber.

6. The fluidic oscillator of claim 5, wherein the oblique angle is in the range of 30 to 45 degrees.

7. The fluidic oscillator of claim 6, wherein the oblique angle is 30 degrees.

* * * * *